United States Patent [19]
Wickersheim

[11] 3,936,196
[45] Feb. 3, 1976

[54] FLUID CHAMBER HAVING MANIPULATABLE WINDOW ELEMENTS

[75] Inventor: Kenneth A. Wickersheim, Palo Alto, Calif.

[73] Assignee: Spectrotherm Corporation, Santa Clara, Calif.

[22] Filed: Oct. 21, 1974

[21] Appl. No.: 516,183

[52] U.S. Cl. .................... 356/246; 73/331; 126/200
[51] Int. Cl.² ............................................. G01N 1/10
[58] Field of Search... 356/181, 246; 350/62, 319 UX, 350/247; 73/196, 324, 334

[56] References Cited
UNITED STATES PATENTS

| | | | |
|---|---|---|---|
| 3,307,400 | 12/1967 | LeRoy | 350/319 X |
| 3,385,285 | 5/1968 | King | 350/319 UX |
| 3,518,009 | 7/1970 | Shamos et al. | 356/181 |

Primary Examiner—Alfred E. Smith
Assistant Examiner—B. W. de los Reyes
Attorney, Agent, or Firm—Limbach, Limbach & Sutton

[57] ABSTRACT

An opaque fluid chamber having some means for filling and removing fluid therefrom and at least one aperture therein having a transparent plate sealing it, thereby permitting light to enter or leave the chamber through said aperture without losing fluid material therethrough. The transparent plate is many times larger than the size of the aperture and selectively clamped thereagainst in a manner permitting removal of a fogged area of the transparent member away from the aperture for continued light transfer into and out of the chamber without having to clean or replace the transparent plate.

2 Claims, 4 Drawing Figures

FLUID CHAMBER HAVING MANIPULATABLE WINDOW ELEMENTS

This invention relates generally to opaque fluid chambers wherein optical examination of the interior thereof is desired through a small aperture. In a preferred form, the invention is, more specifically, directed to such fluid chambers that are designed and utilized with interferometers or spectrometers. In such devices, its desired to pass en electromagnetic energy radiation beam through the fluid chamber. The radiation beam generally enters the chamber through one fluid tight transparent opening and exits from the chamber in an opposite wall through a second fluid tight transparent opening. The characteristics of the beam emerging from the fluid cell are then analyzed to determine the composition of the fluid within the chamber through which the radiation beam has passed.

Such fluid chamber windows have an interior surface in contact with fluid when the chamber is filled. With certain fluids, especially with certain gaseous materials that are investigated, a clouding or fogging of the transparent window inside surface occurs. The accuracy of the results obtained by light transmission through such a fogged window is thus impaired. Presently, the transparent windows are made to be removable from the fluid cell structure. When such a window becomes fogged, it is removed for cleaning unless the fogging has harmed the surface window, in which case the window must be polished or a new window used. When the clean window is replaced, a subsequent test can be conducted with that fluid chamber. This complete disassembly and cleaning, polishing or replacement takes a considerable amount of time. The surfaces of certain window materials, such as sodium chloride, may be so severely damaged by certain fluids as to require the aforementioned window replacement or repolishing and this can be quite expensive.

Therefore, it is a primary object of the present invention to provide a fluid cell with an improved transparent window structure that reduces the required frequency of cleaning or replacement of the window to maintain a light transmittive area free of fogging.

SUMMARY OF THE INVENTION

This and additional objects are accomplished by the present invention wherein a fluid cell includes a pair of small apertures on opposite walls of an opaque housing, each of the apertures being provided with a transparent window that is sealable thereover. The window has an area many times larger than the area of the aperture itself. The window is held over its respective aperture by a mechanism that permits it to be moved with respect to the aperture to provide a clean area for covering the aperture once an existing area has become fogged. The window is moved in this manner after each fogging occurance until nearly the entire surface becomes fogged, at which time it must be removed and cleaned, repolished or replaced. However, such cleaning, polishing or replacement need only occur at very infrequent intervals compared with the amount of such activity required with existing cells that may incur the same amount of use. The replacement cost of cell windows is also reduced.

This has only briefly outlined the principal aspect of the present invention. Additional objects, advantages and features of the present invention will become apparent from the following description which should be taken in conjunction with the accompanying drawings.

DESCRIPTION OF A PREFERRED EMBODIMENT

Figure 1:
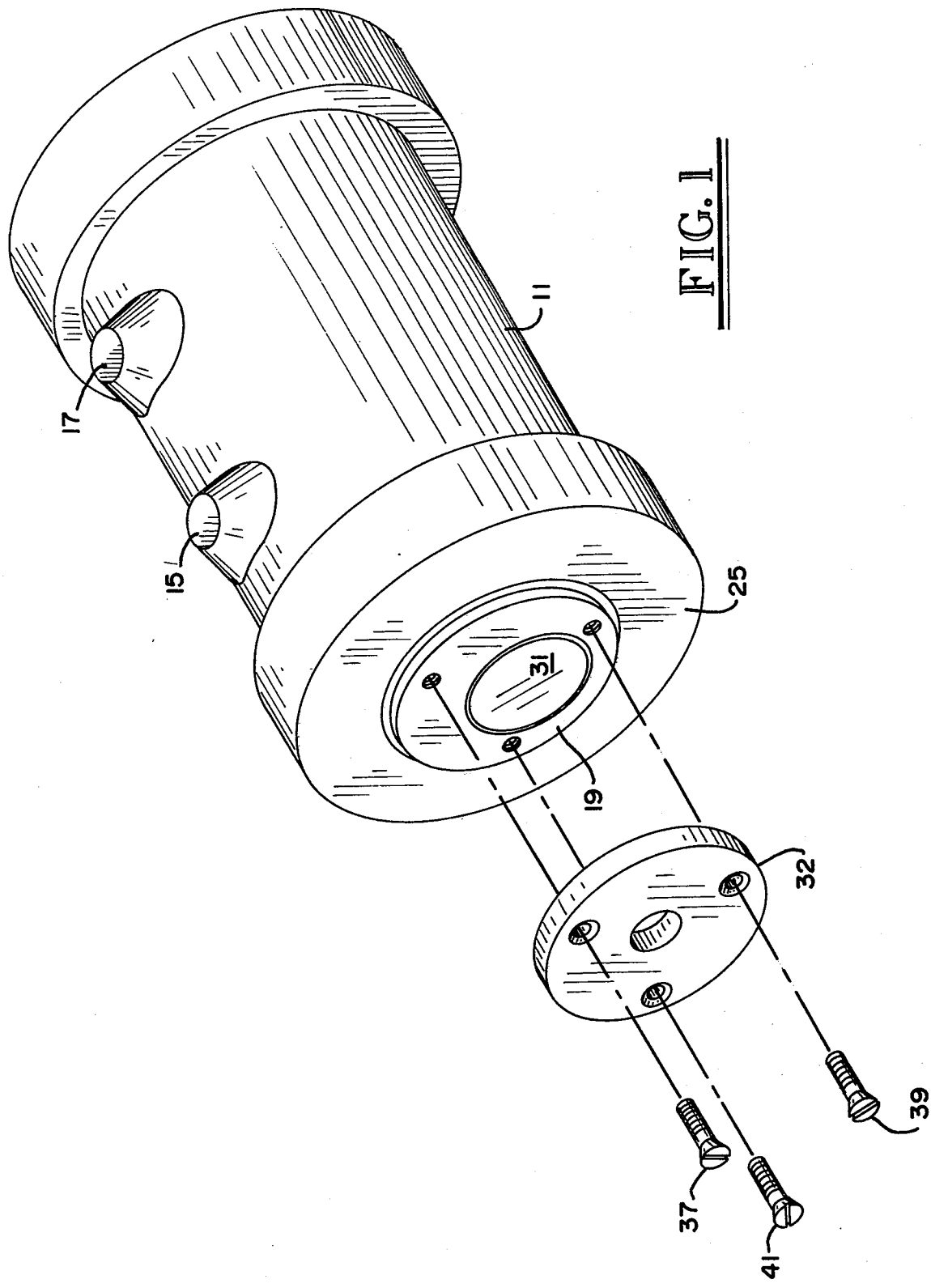
FIG. 1 illustrates in a partly exploded view a fluid cell that includes the improved window structure of the present invention.

The fluid cell illustrated in the drawings includes a solid case 11 forming an elongated fluid chamber 13 therein. There are also provided through the walls of the housing 11 two ports 15 and 17. Fluid material is introduced into and removed from the chamber 13 through these ports. In a specific application of the cell structure described, gaseous materials are continuously passed through the chamber 13, being introduced through one of the ports 15 and 17 and being removed from the chamber 13 through the other of said ports.

The main housing element 11 is opened at both ends. These end openings are each closed by the same type of structure embodying a transparent window construction of the present invention. Only one of these end structures will be described since the other is the same. An end member 19 is positioned between resilient gaskets 21 and 23 and urged against one end of the fluid cell housing 11 by a clamping member 25. A notch provided in the inside surface of the housing member 11 at that end receives the end member 19. The end member 19 is shaped to fill the entire opening of the chamber 13 at that end. The gaskets 21 and 23 in a tight relationship between the parts provide a fluid tight seal therebetween. The housing 11 and the end member 19 are opaque to light transmission.

A small aperture 27 is provided at the center of the end member, and preferably has a circular shape with an opening with a diameter in the order of one millimeter. Attached to an outside surface of the end member 19 about the aperture 27 is a circular gasket 29. A circular piece 31 of flat transparent material provdes the window into the chamber 13 and is normally urged tightly against the gasket 29 by an outer clamping member 32. This contact of the window 31 and the gasket 29 provides a fluid tight seal of the aperture 27. A resilient element 33 is attached to the clamping member 32 for contacting the window 31 to prevent its scratching. The outer clamping member 32 has an aperture 35 therein and is removably attached to the end member 19 by three screws 37, 39 and 41. The transparent window element 31 is held only by compression between the gaskets 29 and 33 and is free to be removed or rotated when the outer clamping member 32 is removed. The material for the window 31 is chosen to be as transparent as possible to the illuminating radiation, such as glass for visible light wavelengths and potassium chloride for infrared radiation wavelengths.

A cylindrical cavity is formed in the outside surface of the end member 19 in a particular manner to accommodate the circular window element 31. A cylindrical wall portion 43 is provided to form a window receiving cavity with a planar end surface 45 adjacent the aperture 27. The cylindrical wall 43 has an axis 47 which is purposely displaced a distance from a center of curvature 49 of the aperture 27. Furthermore, the axis 47 is positioned over the planar wall portion 45 a distance removed from the aperture 27.

Such an offsetting of the axis 47 and center 49 permits rotation of the transparent window 31, when unclamped, with respect to the end plate 19 to remove a fogged interior surface from blocking radiation from traveling through the aperture 27. A clean surface area of the window 31 replaces the fogged region over the aperture 27. Such rotation can be done several times before there is no longer a significantly large clean area of the window 31 that can be positioned over the aperture 27. The window element 31 can then be removed and cleaned. Of course, the diameter of the window element 31 is slightly less than that of the cylndrical surface 43 so that window may be freely rotated therein. FIG. 1 shows the end plate 32 removed, a condition which then permits rotation by hand of the window 31.

The window 31 has a diameter at least twice that of the aperture 27, and preferably several times that of the aperture. For a predominate use of the cell, where the chamber 13 contains gaseous material at a low pressure, the fogging of the window 31 is limited substantially to an area behind the aperture 27, regardless of how close or far the gasket 29 is positioned from the aperture 27.

For very high gas pessure applications of the cell, however, the seal 29 is preferably positioned as close as possible around the edge of the aperture 27 in order to minimize any unnecessary window fogging. For such high gas pressure applications, the seal is positioned to extend a maximum distance beyond the axis 47 to where the axis 47 is equidistant between the outer edges of the gasket 29 and aperture 27 along a line including the axis 47 and aperture center 49. In either case, the seal 29 is most conveniently made in a circular shape.

Figure 2:
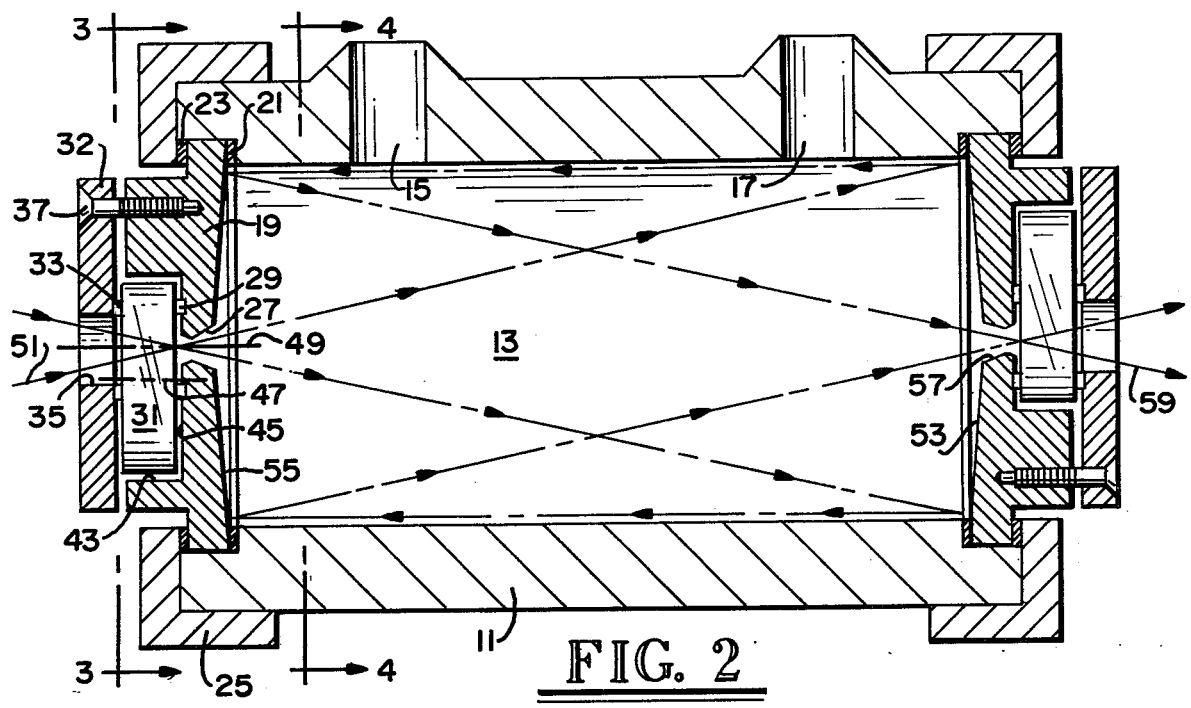
FIG. 2 illustrates a vertical sectional view of the improved fluid cell shown in FIG. 1.
Figure 3:
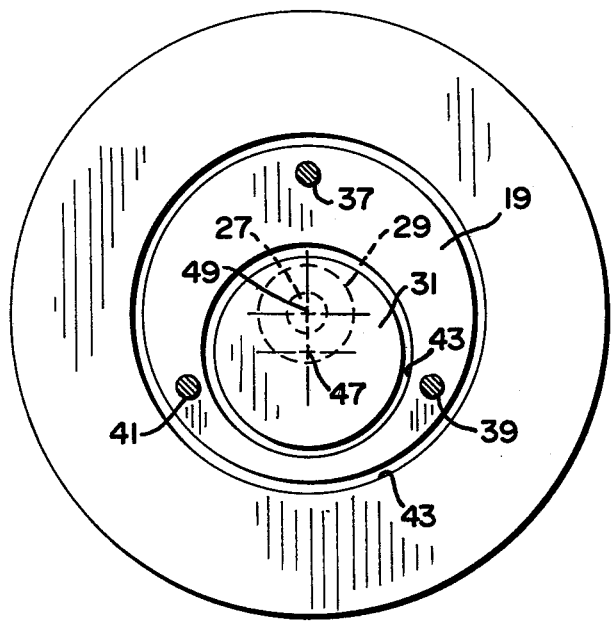
FIG. 3 is a cross-sectional view of the fluid cell of FIGS. 1 and 2 taken at section 3—3 of FIG. 2.
Figure 4:
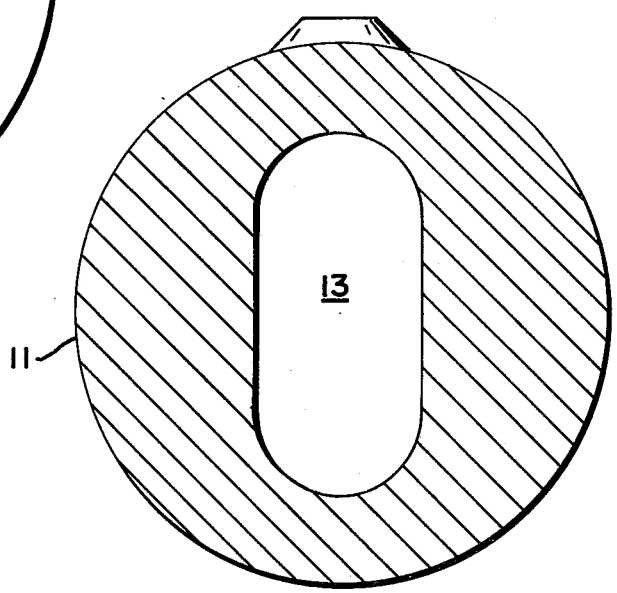
FIG. 4 is a sectional view of the fluid cell of FIGS. 1 and 2 taken at section 4—4 of FIG. 2.

Referring to FIG. 2, the use of a fluid cell as described hereinabove is illustrated with respect to electromagnetic energy radiation rays that are shown in dashed outline. A radiation beam 51 is converged by appropriate optics (not shown) to a substantial point focus at the center of the aperture 27. The beam thus is permitted to enter the chamber 13 through a very small aperture 27. The beam diverges as it crosses the length of the chamber 13 until it strikes a concave mirror surface 53 provided at the opposite end thereof. The mirror surface 53 is shaped to collimate the radiation and reflect it back to the entrance and where it strikes a similar concave reflective surface 55. The surface 55 is shaped to focus the collimated radiation beam into a point focus at an exit aperture 57. A radiation beam 59 exiting from the cell thus contains information as to the characteristics of fluid material within the cell.

The various aspects of the present invention have been described with respect to a specific example thereof but it should be understood that the invention is entitled to protection within the full scope of the appended claims. Many modifications and variations of the specific example described hereinabove are possible. For instance, a cell can be designed with only one radiation opening thereinto, the internal structure being provided with appropriate reflective elements so that an exit radiation beam passes through the same window as the entrance radiation beam. Yet another variation is a single windowed fluid cell with an internal radiation source.

I claim:

1. A fluid containing cell, comprising:

an opaque fluid enclosure having an opening therein for introduction and removal of fluid therefrom and additionally having at least two small apertures therethrough on opposite walls thereof, a circular transparent window element provided for each of said apertures, each of said window elements having an area at least several times that of its associated aperture, and means associated with each of said apertures for selectively holding its associated circular window element in a fluid tight relationship thereagainst with a center of the circular window element being removed from coincidence with its associated aperture, whereby the holding means may be released to permit rotation of the circular window element when it becomes fogged in an area covering its associated aperture and thereby to permit a clean window area to be positioned over said aperture and resealed thereto without having to clean the window.

2. An opaque elongated enclosed chamber comprising at each end thereof:

a planar end wall segment having a circular aperture therein opening the inside of said chamber to the outside, a fluid sealing material held by said end wall portion around said circular aperture, a cylindrical wall structure extending outward from the planar end wall portion to form a cylindrical receptacle having a diameter at least twice the diameter of said aperture, said wall having an axis positioned over said planar end wall portion and displaced a distance from said aperture, a circularly shaped radiation transmittive element positionable in said cylindrical receptacle, and means manually releasable for clamping the transmittive element against said seal, whereby said transmittive element may be disengaged from sealing the circular aperture and rotated to present a clean area thereof over said aperture and resealed to the planar surface.

* * * * *